US009410874B2

(12) United States Patent
He et al.

(10) Patent No.: US 9,410,874 B2
(45) Date of Patent: Aug. 9, 2016

(54) SIMULATED IMPACT-TYPE ROCK BURST EXPERIMENT APPARATUS

(75) Inventors: Manchao He, Beijing (CN); Xuena Jia, Beijing (CN); Dongqiao Liu, Beijing (CN)

(73) Assignee: China University of Mining & Technology (Beijing), Beijing (CN)

( * ) Notice: Subject to any disclaimer, the term of this patent is extended or adjusted under 35 U.S.C. 154(b) by 15 days.

(21) Appl. No.: 14/389,338

(22) PCT Filed: Mar. 31, 2012

(86) PCT No.: PCT/CN2012/073440
§ 371 (c)(1),
(2), (4) Date: Sep. 29, 2014

(87) PCT Pub. No.: WO2013/143152
PCT Pub. Date: Oct. 3, 2013

(65) Prior Publication Data
US 2015/0168282 A1    Jun. 18, 2015

(51) Int. Cl.
*G01N 3/24* (2006.01)
*G01N 3/313* (2006.01)
*G01N 3/08* (2006.01)

(52) U.S. Cl.
CPC .................. *G01N 3/24* (2013.01); *G01N 3/313* (2013.01); *G01N 3/08* (2013.01); *G01N 2203/0256* (2013.01)

(58) Field of Classification Search
CPC ... G01N 2203/0256; G01N 3/08; G01N 3/24; G01N 3/13
USPC ........................................... 73/784, 841, 803
See application file for complete search history.

(56) References Cited

U.S. PATENT DOCUMENTS

| 4,444,058 | A | | 4/1984 | Ratigan | |
|---|---|---|---|---|---|
| 5,025,668 | A | * | 6/1991 | Sarda | G01N 3/10 73/795 |
| 5,025,669 | A | * | 6/1991 | Sarda | G01N 3/10 73/798 |
| 5,063,785 | A | * | 11/1991 | Labuz | G01N 3/10 73/821 |

(Continued)

FOREIGN PATENT DOCUMENTS

| CN | 101051011 A | 10/2007 |
|---|---|---|
| CN | 101140207 A | 3/2008 |

(Continued)

OTHER PUBLICATIONS

He M C et al. "rock burst process of limestone and its acoustic emission characteristics under true-triaxial unloading conditions," *International Journal of Rock Mechanics and Mining Sciences*, vol. 47, No. 2, Feb. 1, 2010, pp. 286-298.

(Continued)

*Primary Examiner* — Max Noori
(74) *Attorney, Agent, or Firm* — Yunling Ren; Eaton & Van Winkle (57) ABSTRACT

A simulated impact-type rock burst experiment apparatus includes a bracket, a specimen box assembly, an X-direction, Y-direction and Z-direction loading mechanisms mounted on the bracket, and control systems. Each loading mechanism includes four supporting posts in a rectangular arrangement, a first and second frames aligned with each other and fixedly connected to both ends of the four supporting posts, a loading hydraulic cylinder and a lead screw mounted on the two frames respectively.

19 Claims, 5 Drawing Sheets

(56) References Cited

U.S. PATENT DOCUMENTS

| | | | | |
|---|---|---|---|---|
| 5,265,461 | A | * | 11/1993 | Steiger .................. G01N 29/07 73/38 |
| 2009/0000361 | A1 | * | 1/2009 | Bloomquist ............. G01N 3/24 73/86 |
| 2011/0107844 | A1 | * | 5/2011 | Secq ....................... E21B 21/08 73/825 |

FOREIGN PATENT DOCUMENTS

| | | |
|---|---|---|
| CN | 101718660 A | 6/2010 |
| JP | 62124446 | 8/1987 |
| JP | 6146866 | 11/1987 |
| JP | 10206303 | 8/1998 |
| JP | 2001337014 | 12/2001 |
| JP | 2002195924 | 7/2002 |
| JP | 2007333671 | 12/2007 |
| SU | 1285340 A2 | 1/1987 |
| SU | 1298593 A1 | 3/1987 |

OTHER PUBLICATIONS

Supplementary European Search Report Application No. EP 12872655, dated Mar. 31, 2015.

Jinli Miao, "Experimental Analysis on the Energy Characteristics of Rockburst", Doctorate Dissertation of China University of Mining & Technology (Beijing), 2009, pp. 19-33.

Manchao HE et. all, "Experimental Study on Rockburst Processes of Granite Specimen at Great Depth", Chinese Jornal of Rock Mechanics and Engineering, May 2007, pp. 865-875, vol. 26.

Manchao HE et. all, "Experimental Study on Rockburst Processes of Granite at Great Depth", Centennial Anniversary Symposium of China UNV of Mining & Technology (Beijing), 2009.

Office Action issued Sep. 15, 2015 by the JP Office.

* cited by examiner

SIMULATED IMPACT-TYPE ROCK BURST EXPERIMENT APPARATUS

CROSS-REFERENCE TO RELATED PATENT APPLICATIONS

This application is a national phase of the international application PCT/CN2012/073440, filed Mar. 31, 2012 under 35 USC §371, which is incorporated by reference in its entirety.

TECHNICAL FIELD

The present disclosure relates to a field of deep mine engineering rock mass mechanics and geotechnical engineering research, in particular to a simulated impact-type rock burst experiment apparatus.

BACKGROUND

Since geotechnical engineering such as mining, hydropower, railways (road) traffic tunnel, etc., are developing toward deep, a rockburst as a sort of dangerous disaster phenomenon in deep mines is happening more and more frequently. The rockburst has a nature of suddenness and violence, and when it breaks, shot rock fragments carrying with a large amount of energy threaten equipment and people, and serious one even endanger lives.

It is well known that a blasting is an indispensable construction measure for a rock excavation in recent large-scale water conservancy, tunnel, mining engineering and nuclear power engineering. When explosive blasts in a rock mass, it releases a large amount of explosive energy in a moment, generates a blasting shock wave and a stress wave which act on the surrounding rock mass in a form of a dynamic load, to make the surrounding rock mass be broken and damaged, and even generate a rockburst. However, conventional experimental apparatus for rock sample specimen have low stiffness, thereby the forces in X, Y and Z direction cannot be accurately guaranteed to be applied vertically, which fails to induce the phenomenon of rockburst, and affects analysis and research of the rockburst mechanism.

SUMMARY

The object of the present disclosure is to solve the defects in prior art, and to provide a simulated impact-type rock burst experiment apparatus with good stiffness.

To achieve the above object, the present disclosure adopts technical solutions as follows:

In one aspect, the present disclosure provides a simulated impact-type rock burst experiment apparatus comprising a bracket, a specimen box assembly, X-direction, Y-direction and Z-direction loading mechanisms mounted on the bracket, three sets of independent control systems for controlling the X-direction, Y-direction and Z-direction loading mechanisms respectively. Wherein, the X-direction loading mechanism comprises four X-direction supporting posts in a rectangular arrangement; a first X-direction frame mounted on the bracket and fixedly connected to one end of the four X-direction supporting posts; a second X-direction frame mounted on the bracket and fixedly connected to the other end of the four X-direction supporting posts and aligned with the first X-direction frame; an X-direction loading hydraulic cylinder fixedly mounted at a center position of the first X-direction frame; and an X-direction lead screw mounted at a center position of the second X-direction frame with a center line thereof in line with a center line of a piston rod of the X-direction loading hydraulic cylinder, wherein an X-direction adjusting handle wheel is provided at an outer end of the X-direction lead screw, and an X-direction sensor is provided at an inner end of the X-direction lead screw. The Y-direction loading mechanism comprises four Y-direction supporting posts in a rectangular arrangement and mounted on the bracket; a first Y-direction frame fixedly connected to one end of the four Y-direction supporting posts; a second Y-direction frame fixedly connected to the other end of the four Y-direction supporting posts, and aligned with the first Y-direction frame; a Y-direction loading hydraulic cylinder fixedly mounted at a center position of the first Y-direction frame; and a Y-direction lead screw mounted at a center position of the second Y-direction frame with a center line thereof in line with a center line of a piston rod of the Y-direction loading hydraulic cylinder; wherein an operating wheel is provided at an outer end of the Y-direction lead screw, and a Y-direction sensor is provided at an inner end of the Y-direction lead screw. The Z-direction loading mechanism comprises four Z-direction supporting posts in a rectangular arrangement; a first Z-direction frame mounted on the bracket and fixedly connected to one end of the four Z-direction supporting posts; a second Z-direction frame mounted on the bracket and fixedly connected to the other end of the four Z-direction supporting posts, and aligned with the first Z-direction frame; a Z-direction loading hydraulic cylinder fixedly mounted at a center position of the first Z-direction frame; a Z-direction lead screw mounted at a center position of the second Z-direction frame with a center line thereof in line with a center line of a piston rod of the Z-direction loading hydraulic cylinder; wherein a Z-direction adjusting handle wheel is provided at an outer end of the Z-direction lead screw, and a Z-direction sensor is provided at an inner end of the Z-direction lead screw; wherein extension lines of center lines of piston rods of X, Y and Z-direction loading hydraulic cylinders intersect at a same center point, and the specimen box assembly is disposed on the bracket with a center of the specimen box assembly coincident with the same center point.

According to one embodiment of the present disclosure, wherein two pairs of X-direction guide rails are provided on the bracket, a pair of first X-direction legs are provided under the first X-direction frame in which a first X-direction roller is mounted under each first X-direction leg; a pair of second X-direction legs are provided under the second X-direction frame in which a second X-direction roller is mounted under each second X-direction leg, the two first X-direction rollers and the two second X-direction rollers cooperate with the two pairs of X-direction guide rails respectively.

According to one embodiment of the present disclosure, wherein two pairs of Z-direction guide rails are provided on the bracket, a pair of first Z-direction legs are provided under the first Z-direction frame in which a first Z-direction roller is mounted under each first Z-direction leg; a pair of second Z-direction legs are provided under the second Z-direction frame in which a second Z-direction roller is mounted under each second Z-direction leg, the two first Z-direction rollers and the two second Z-direction rollers cooperate with the two pairs of Z-direction guide rails respectively.

According to one embodiment of the present disclosure, wherein the bracket comprises a base and a work platform in a horizontal state and fixedly mounted on the base by a post, the first X-direction frame, the second X-direction frame, the four Y-direction supporting posts, the first Z-direction frame and the second Z-direction frame are mounted on the work platform, and the second Y-direction frame is located in a space between the work platform and the base.

According to one embodiment of the present disclosure, wherein the Y-direction supporting posts are arranged in vertical direction with lower ends thereof pass through the bracket; nuts are respectively engaged with lower parts of the Y-direction supporting posts; compression springs are respectively sleeved around the lower parts of the Y-direction supporting posts with an upper end against the nut and a lower end against the bracket.

According to one embodiment of the present disclosure, wherein a Y-direction adjusting handle wheel is provided at a side surface of the second Y-direction frame, which is coupled with the operating wheel through a transmission chain.

According to one embodiment of the present disclosure, wherein the control system comprising a plurality of sensors used for collecting displacement, amount of deformation of or value of force acting on the rock sample specimen, respectively; a hydraulic source comprising a pump station used for supplying hydraulic oil for X, Y and/or Z-direction loading hydraulic cylinders, and a servo valve comprising at least one adjusting valve and at least one reversal valve; and a controller used to equalize the displacement of or force acting on each piston rod of X, Y and/or Z-direction loading hydraulic cylinders and amount of force, displacement or deformation represented by the input dynamic load signal, by receiving data collected by the plurality of sensors, evaluating difference by comparing the received data with a given dynamic load signal, performing correction adjustment based on the difference to control opening amount of the adjusting valve, and in turn to control the amount and rate of oil intake or oil output of X, Y and/or Z-direction loading hydraulic cylinders to further control displacement of or force acting on each piston rod of X, Y and/or Z-direction loading hydraulic cylinders, and controlling the reversal valve to reverse.

According to one embodiment of the present disclosure, wherein the specimen box assembly comprises a frame and 6 press plates. The frame is composed of 12 arrises for housing a rock sample specimen and in a shape of cube or rectangular parallelepiped. The 6 press plates correspond to the 6 windows of the frame respectively. Each press plate comprises a press plate body having a loading surface towards the interior of the frame and an abutment surface opposite to the loading surface. The dimension of the loading surface of the press plate is smaller than that of the window of the frame. One hitch is formed at a center of each peripheral side of the press plate, one restricting element is provided at a center of each arris of the frame, and the press plate is hitched to the frame through the hitch and the restricting element.

According to one embodiment of the present disclosure, wherein the dimension of the abutment surface is larger than or equal to that of the window of the frame; and each loading surface of the press plate body has a sloped transition surface at the periphery.

According to one embodiment of the present disclosure, wherein the specimen box assembly further comprises 6 friction reducing plates located between the 6 press plates and the rock sample specimen respectively, the friction reducing plate has a thickness of 1-2 mm.

According to one embodiment of the present disclosure, wherein one of the 6 press plates has a center half hole corresponding to an opening of a half hole on the rock sample specimen.

According to one embodiment of the present disclosure, wherein a mounting element is disposed at center of the abutment surface of the press plate having a center half hole; a light transmission slot is provided at the mounting element in which a micro camera is mounted and directed straight towards the center half hole of the press plate.

According to one embodiment of the present disclosure, wherein a pair of press plates of 6 press plates positioned in a same direction has a center half hole respectively corresponding to openings of a through hole in the rock sample specimen.

According to one embodiment of the present disclosure, wherein a mounting element is disposed at center of the abutment surface of one of the pair of press plates having center half hole; a light transmission slot is provided at the mounting element in which a micro camera is mounted; a second mounting element is disposed at center of the abutment surface of the other one of the pair of press plates having center half hole; a second light transmission slot is provided at the second mounting element in which a focus lamp is mounted, both the micro camera and the focus lamp are directed straight towards the center half hole of the press plate.

According to one embodiment of the present disclosure, wherein the specimen box assembly further comprises a specimen box trolley which comprises a flat plate and two pairs of wheels mounted at two sides of the flat plate; the two pairs of wheels cooperate with two of the four X-direction supporting posts in lower position, or with two of the four Z-direction supporting posts in lower position.

According to one embodiment of the present disclosure, wherein a through hole is provided at center of the flat plate which is adapted to install a vertical direction lead screw.

According to one embodiment of the present disclosure, wherein the through hole of the flat plate is in a circular shape with a diameter 1-10 mm larger than that of the vertical-direction lead screw.

According to one embodiment of the present disclosure, wherein the through hole is in rectangular shape, and distance between a pair of opposite sides of the through hole is 1-10 mm larger than the diameter of the vertical-direction lead screw.

According to one embodiment of the present disclosure, wherein a restricting frame is mounted at an inner edge of the through hole on the flat plate of the specimen box trolley, and a distance between a pair of opposite sides of the restricting frame is 1-10 mm larger than a diameter of the vertical direction lead screw.

In accordance with the above technical solution, it can be seen that, advantages and positive effects of the simulated impact-type rock burst experiment apparatus of the present disclosure lie in that the body structure of the present disclosure includes X-direction, Y-direction and Z-direction loading mechanisms which are able to exert static and dynamic load to the rock sample specimen in three directions perpendicular with each other, and therefore can be used to perform experimental method for simulating an impact rockburst. Furthermore, the structures of X-direction, Y-direction and Z-direction loading mechanisms are substantially the same, which have good symmetry, therefore, it is easy to accurately control the operation of exerting static or dynamic load to the rock sample specimen in the three directions. Particularly, each loading mechanism includes four supporting posts in a rectangular arrangement, which is able to improve stiffness of the apparatus and loading accuracy in three directions.

By the following illustrations on the preferred embodiments of the present disclosure with reference to accompanying drawings, the above and other objects, features and advantages of the present disclosure will become more distinct.

DETAILED DESCRIPTION

The embodiments of the present disclosure will be illustrated in detail as follows. Here the described embodiments are used to illustrate the present disclosure, but not used to limit the present disclosure.

In the simulated impact-type rock burst experiment apparatus according to the embodiments of the present disclosure, a direction of axis X, a direction of axis Y, and a direction of axis Z are perpendicular to one another to construct a three-dimension space. The direction of axis X and the direction of axis Z are in a horizontal directions, and the direction of axis Y is in a vertical direction.

Figure 1:
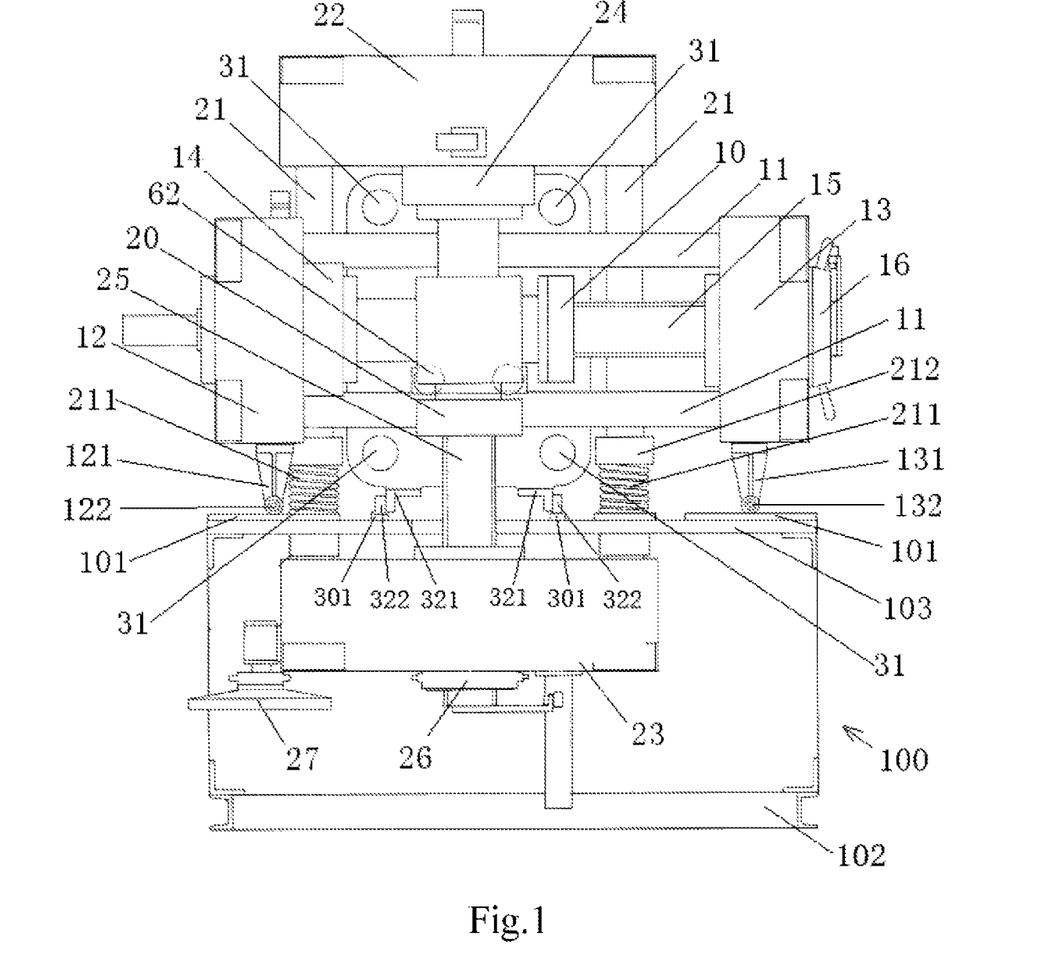
FIG. 1 is a structural schematic view of the simulated impact-type rock burst experiment apparatus according to the present disclosure.
Figure 2:
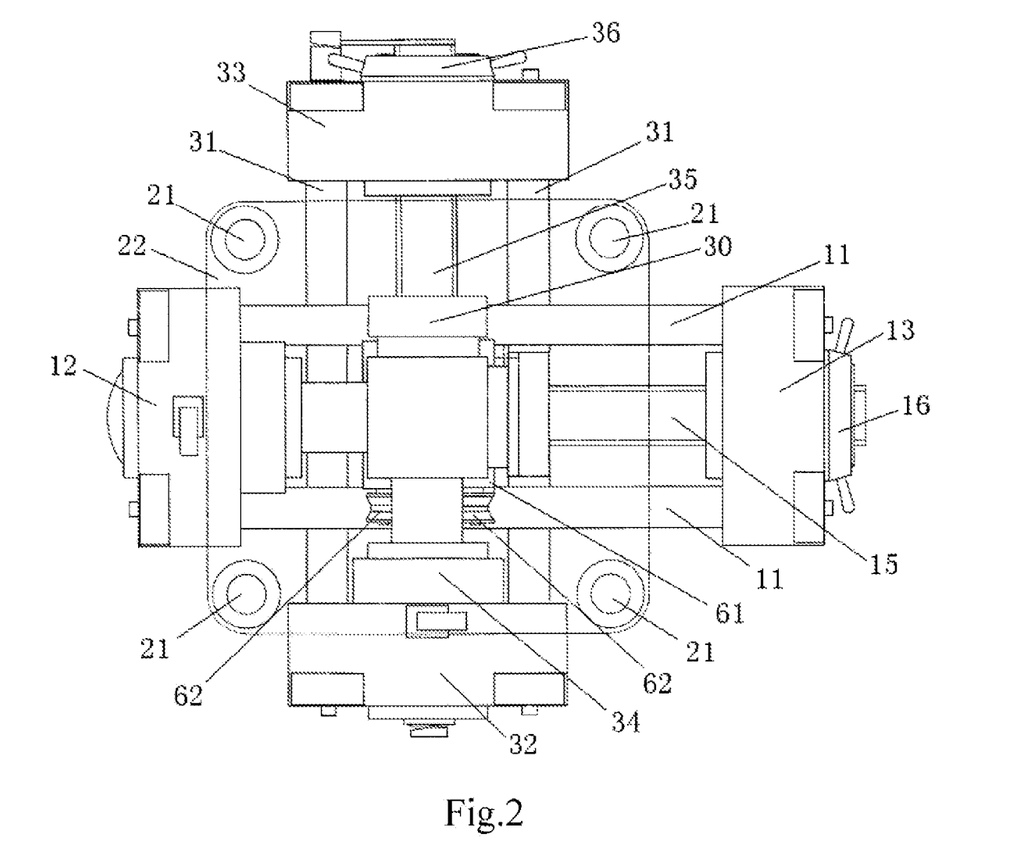
FIG. 2 is a top view of the simulated impact-type rock burst experiment apparatus as shown in FIG. 1.

As shown in FIGS. 1 and 2, the simulated impact-type rock burst experiment apparatus according to the present disclosure includes a bracket 100, a specimen box assembly, an X-direction, Y-direction and Z-direction loading mechanisms mounted on the bracket 100, control systems for controlling the X-direction, Y-direction and Z-direction loading mechanisms and a power system.

The bracket 100 includes a base 102 located on the ground and a work platform 103 in a horizontal state and fixedly mounted on the base 102 by a post or a supporting plate. There is a space with a certain height between the work platform 103 and the base 102. However, the structure of the bracket 100 is not limited thereto, any other prior structure may also be applied in the present disclosure.

The X-direction loading mechanism includes four X-direction supporting posts 11, a first X-direction frame 12, a second X-direction frame 13, a X-direction loading hydraulic cylinder 14 and a X-direction lead screw 15. The four X-direction supporting posts 11 are arranged horizontally and parallel to each other in a rectangular arrangement. The first X-direction frame 12 is mounted on the work platform 103 of the bracket 100 and fixedly connected to one end of the four X-direction supporting posts 11. The second X-direction frame 13 is mounted on the work platform 103 of the bracket 100, fixedly connected to the other end of the four X-direction supporting posts 11, and is aligned with the first X-direction frame 12. The X-direction loading hydraulic cylinder 14 is fixedly mounted at a center position of the first X-direction frame 12 in which a piston rod thereof towards the second X-direction frame 13. The X-direction lead screw 15 is mounted at a center position of the second X-direction frame 13 with a center line thereof in line with a center line of the piston rod of the X-direction loading hydraulic cylinder 14. An X-direction adjusting handle wheel 16 is provided at an outer end of the X-direction lead screw 15 for driving the X-direction lead screw 15. An X-direction sensor 10 is provided at an inner end of the X-direction lead screw 15 for sensing a value of stress (or strain) exerted in X direction.

The Y-direction loading mechanism includes four Y-direction supporting posts 21, a first Y-direction frame 22, a second Y-direction frame 23, a Y-direction loading hydraulic cylinder 24 and a Y-direction lead screw 25. The four Y-direction supporting posts 21 have a rectangular arrangement and are mounted on the work platform 103 of the bracket 100. The first Y-direction frame 22 is fixedly connected to one end of the four Y-direction supporting posts 21. The second Y-direction frame 23 is fixedly connected to the other end of the four Y-direction supporting posts 21, and is aligned with the first Y-direction frame 22. The Y-direction loading hydraulic cylinder 24 is fixedly mounted at a center position of the first Y-direction frame 22 in which a piston rod thereof towards the second Y-direction frame 23. The Y-direction lead screw 25 is mounted at a center position of the second Y-direction frame 23 with a center line thereof in line with a center line of the piston rod of the Y-direction loading hydraulic cylinder 24. An operating wheel 26 is provided at an outer end of the Y-direction lead screw 25 for driving the Y-direction lead screw 25. The operating wheel 26 mounted under the second Y-direction frame 23 is inconvenient to be operated. In this case, a Y-direction adjusting handle wheel 27 is provided at a side surface of the second Y-direction frame 23, which is coupled with the operating wheel 26 through a transmission chain. It is convenient to drive the Y-direction lead screw 25 by the cooperation of the Y-direction adjusting handle wheel 27, transmission chain and the operating wheel 26. A Y-direction sensor 20 is provided at an inner end of the Y-direction lead screw 25 for sensing a value of stress (or strain) exerted in Y direction.

In an embodiment of the present disclosure, the second Y-direction frame 23 is located in a space between the work platform 103 and the base 102, which reduces the overall volume of the apparatus and lowers the center of gravity in the apparatus so as to improve stability. In the present embodiment, the Y-direction supporting posts 21 are fixedly connected to the work platform 103 of the bracket 100 in a manner of welding or the like with the lower end of the Y-direction supporting posts 21. Another connection manner is that the work platform 103 has openings corresponding to each Y-direction supporting post 21 for the lower ends of the Y-direction supporting posts 21 to pass through. Each Y-direction supporting post 21 has thread at lower part, and a nut 212 above the work platform 103 is engaged with the thread. A compression spring 211 is sleeved around the lower part of the Y-direction supporting post 21 with an upper end against the nut 212 and a lower end against the bracket 100. The compression spring 211 has a good cushioning and vibration absorbing effect, and the first Y-direction frame 22 is able to be maintained in a horizontal state by adjusting the nut 212, such that the rock sample specimen is always loaded by the Y-direction loading hydraulic cylinder 24 in a perpendicular direction.

The Z-direction loading mechanism includes four Z-direction supporting posts 31, a first Z-direction frame 32, a second Z-direction frame 33, a Z-direction loading hydraulic cylinder 34 and a Z-direction lead screw 35. The four Z-direction supporting posts 31 have a rectangular arrangement. The first Z-direction frame 32 is mounted on the work platform 103 of the bracket 100 and fixedly connected to one end of the four Z-direction supporting posts 31. The second Z-direction frame 33 is mounted on the bracket 100, fixedly connected to the other end of the four Z-direction supporting posts 31, and is aligned with the first Z-direction frame 32. The Z-direction loading hydraulic cylinder 34 is fixedly mounted at a center position of the first Z-direction frame 32 in which a piston rod thereof towards the second Z-direction frame 33. The Z-direction lead screw 35 is mounted at a center position of the second Z-direction frame 33 with a center line thereof in line with a center line of the piston rod of the Z-direction loading hydraulic cylinder 34. A Z-direction adjusting handle wheel 36 is provided at an outer end of the Z-direction lead screw 35 for driving the Z-direction lead screw 35. A Z-direction sensor 30 is provided at an inner end of the Z-direction lead screw 35 for sensing a value of stress (or strain) loading in Z direction.

Extension lines of center lines of piston rods of X, Y and Z-direction loading hydraulic cylinders 14, 24 and 34 intersect at the same center point. During experiment, the specimen box assembly is disposed on the work platform 103 of the bracket 100 with the center of the specimen box assembly coincident with the same center point.

In an embodiment of the present disclosure, two pairs of X-direction guide rails 101 are provided on the work platform 103 of the bracket 100 in X direction. A pair of first X-direction legs 121 is provided under the first X-direction frame 12 in which a first X-direction roller 122 is mounted under each first X-direction leg 121. A pair of second X-direction legs 131 is provided under the second X-direction frame 13 in which a second X-direction roller 132 is mounted under each second X-direction leg 131. One pair of first X-direction rollers 122 and one pair second X-direction rollers 132 cooperate with two pairs of X-direction guide rails 101 respectively, i.e., the first and second X-direction frames 12 and 13 are supported on the bracket by a guide rail-roller set, which allows the first and second X-direction frames 12 and 13 and four X-direction supporting posts 11 to move a distance in X direction, such that it is more convenient and flexible to adjust the extension lines of center lines of piston rods of X, Y and Z-direction loading hydraulic cylinders 14, 24 and 34 to intersect at the same center point, in other words, the specimen box assembly is able to be installed at a center position more conveniently and flexibly.

In an embodiment of the present disclosure, two pairs of Z-direction guide rails 301 are provided on the bracket 100. A pair of first Z-direction legs 321 is provided under the first Z-direction frame 32 in which a first Z-direction roller 322 is mounted under each first Z-direction leg 321. A pair of second Z-direction legs is provided under the second Z-direction frame 33 in which a second Z-direction roller is mounted under each second Z-direction leg. One pair of first Z-direction rollers 322 and one pair of second Z-direction rollers cooperate with two pairs of Z-direction guide rails 301 respectively, i.e., the first and second Z-direction frames 32 and 33 are supported on the bracket by a guide rail-roller set, which allows the first and second Z-direction frames 32 and 33 and four Z-direction supporting posts 31 to move a distance in Z direction, therefore, the specimen box assembly is able to be installed at a center position more flexibly.

Figure 3:
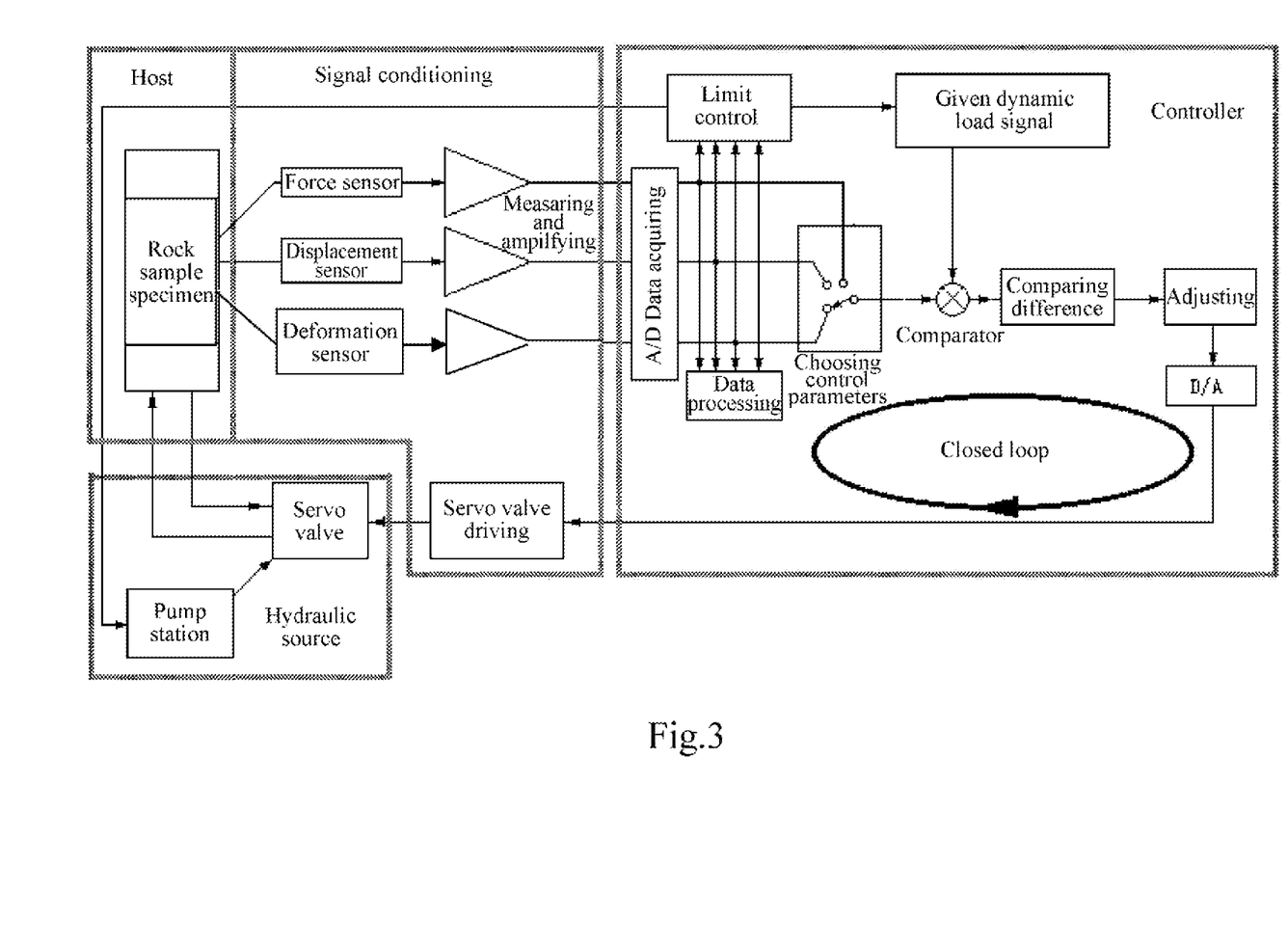
FIG. 3 is a schematic diagram of a control system in the simulated impact-type rock burst experiment apparatus according to the present disclosure.

As shown in FIG. 3, the present disclosure further includes three sets of control systems independent of and coordinating with each other. Each control system has control parameters such as force (stress) and displacement (strain) of actuator. If one of the control parameters is selected, it would constitute a control loop for the selected parameters, and the control parameters not selected (an experiment result to be evaluated) acts as a function of the selected parameter. The control system is completely digitized and controlled by controller. Three control systems are of the same constitution and operating principle. As shown in FIG. 3, the control system includes a plurality of sensors, a hydraulic source and a controller. A plurality of sensors is used for collecting the displacement, amount of deformation or value of force acting on the rock sample specimen respectively. The hydraulic source includes a pump station and a servo valve. The pump station is used for supplying hydraulic oil for X, Y and/or Z-direction loading hydraulic cylinders 14, 24 and 34. The servo valve includes at least one adjusting valve and at least one reversal valve. The controller is used for receiving data collected by the plurality of sensors, evaluating difference by comparing the received data with a given dynamic load signal, revising and adjusting based on the difference, and controlling opening amount of the adjusting valve, thereby controlling the amount and rate of oil intake or output of X, Y and/or Z-direction loading hydraulic cylinders 14, 24 and 34, and further controlling displacement or force acting on each piston rod of X, Y and/or Z-direction loading hydraulic cylinders 14, 24 and 34, meanwhile the controller may control the reversal valve to reverse, finally realizing that the displacement or force acting on each piston rod of X, Y and/or Z-direction loading hydraulic cylinders 14, 24 and 34 is consistent with amount of force, displacement or deformation expressed by the input dynamic load signal.

The control system of the present disclosure further have alarm function. If a value sensed by the sensor exceeds a preset limiting range of control, the controller will shut down the servo valve, cut off oil circuit and discharge oil pressure, thereby preventing the rock sample specimen from accidentally damaged. Meanwhile the pump station will stop working. If a value of given dynamic load signal exceeds a preset limiting range of control, the control system can also alarm. In addition, the control system of the present disclosure can also process data sensed by the sensor: extracting signal value sensed by the sensor and deducing valuable and meaningful data, for example, forming force-time curve, displacement-time curve, stress-strain curve, etc.

In the control system of the present disclosure, large amount of high-pressure oil is output from the hydraulic source and enters into the servo valve. The operator choose control parameters such as experimental force, deformation of the specimen or stroke of the piston and given dynamic load signal according to the experimental purpose. The given dynamic load signal is input into the comparator and compared with a value sensed by the sensor so as to obtain a difference. After the difference is revised, the servo valve which may be a conventional structure, is driven to convert quantity of electricity into quantity of oil-flow so as to drive the piston of the hydraulic cylinder to apply force to the rock sample specimen. Non-electrical physical quantity such as force, deformation or displacement is converted into quantity of electricity by the sensor, and then compared with a given signal in the comparator after amplified. A compared difference may be output and revised by an adjustor, such that the non-electrical physical quantity controlling the rock sample specimen is able to quickly and accurately track the given signal with a certain precision.

The above control system is primarily used for controlling the dynamic load signal applied to the rock sample specimen. However, it is not limited thereto, the other systems in the current structures, such as dynamic load control system or static load control system are possible.

As shown in FIGS. 4 to 7, the specimen box assembly according to the present disclosure includes a frame 4 and 6 press plates 5.

Figure 4:
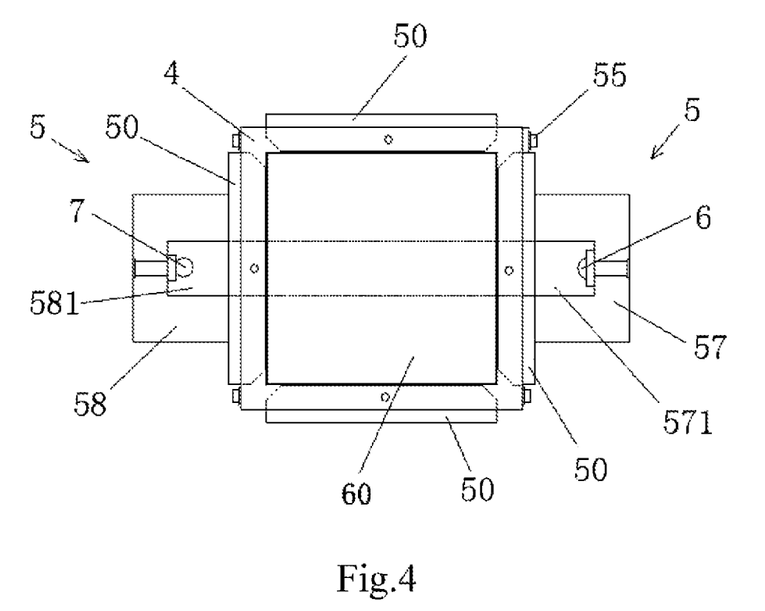
FIG. 4 is a structural schematic view of a specimen box assembly according to the present disclosure.

The frame 4 shaped in a cube is used for housing a rock sample specimen 60. The frame 4 is composed of 12 arrises and has 6 surfaces each of which has a window to expose the rock sample specimen 60. In the present disclosure, the shape of the frame 4 is not limited to a cube, and may also be rectangular parallelepiped and the like.

Figure 5:
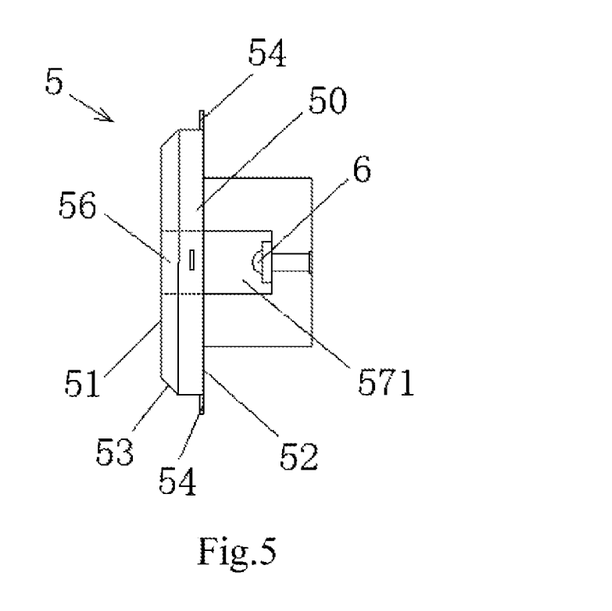
FIG. 5 is a structural schematic view of press plates in the specimen box assembly as shown in FIG. 4.
Figure 6:
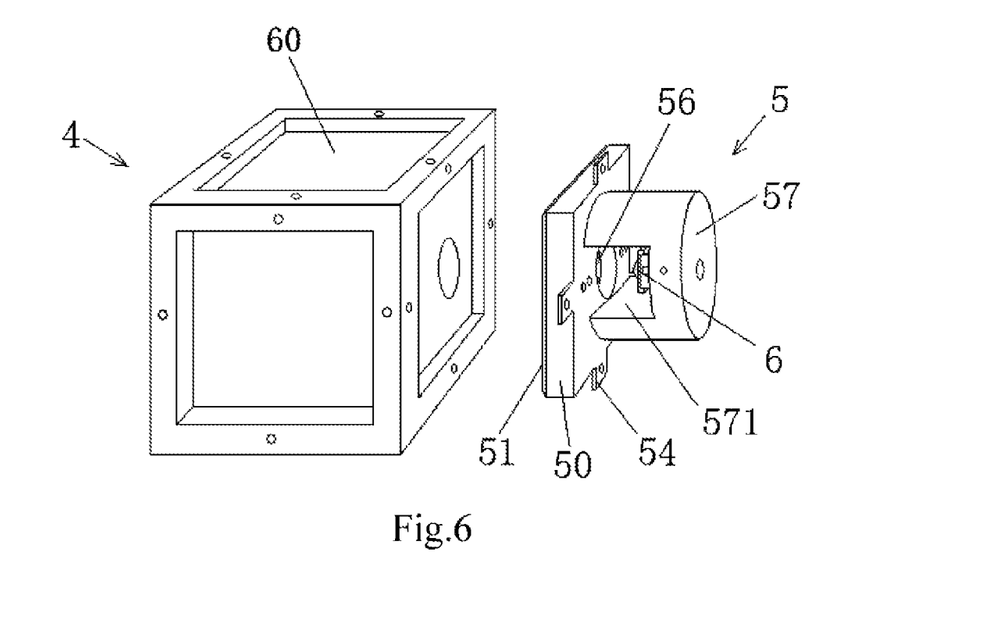
FIG. 6 is a perspective structural view illustrating an engagement of the press plates and a frame in the specimen box assembly.

The 6 press plates 5 correspond to the 6 windows of the frame 4 shaped in a cube respectively. Each press plate 5 includes a press plate body 50 having a loading surface 51 towards the interior of the frame 4 and an abutment surface 52 opposite to the loading surface 51. The dimension of the loading surface 51 of the press plate 5 is smaller than that of the window of the frame 4 so as to allow the loading surface 51 enters into the window of the frame 4 and can against the rock sample specimen 60 during loading. In order to ensure the press plate 5 is aligned with the corresponding window which allows the load to uniformly applied on the rock sample specimen 60, one hitch 54 is formed at the center of each peripheral side of the press plate 5, one restricting element 55, such as positioning bolt, is provided at center of each arris of the frame 4, and the press plate 5 is hitched to the frame 4 with the hitch 54 and restricting element 55. The restricting element 55, such as positioning bolt, can restrict movement or rotation of the press plate 5 perpendicular to the loading direction, without interfering movement of the press plate 5 along the loading direction during applying load to the rock sample specimen 60. In order to reduce friction between the press plate 5 and the rock sample specimen, the specimen box according to the present disclosure further includes 6 friction reducing plates located between the 6 press plates 5 and the rock sample specimen respectively, each of the friction reducing plate has a thickness of 1-2 mm, and may be made of F4-Bronze composites.

The specimen box assembly according to the present disclosure includes 6 press plates 5 and the frame 4 shaped in a cube or rectangular parallelepiped and having bottom plate, therefore, the specimen box assembly is able to apply static and dynamic load from three directions, thereby performing various experiments to the rock sample specimen.

In an embodiment of the present disclosure, the dimension of the abutment surface 52 is larger than or equal to that of the window of the frame 4, and the dimension of the loading surface 51 of the press plate 5 is smaller than that of the window of the frame 4. Each loading surface 51 of the press plate body 50 has a sloped transition surface 53 at the periphery, which has a inclined angle for ensuring enough feeding amount for the press plate 5 during loading. In the present disclosure, the feeding amount is 2-8 mm, and the thickness of the sloped transition surface 53 is substantially equal to the feeding amount (2-8 mm). During loading the rock sample specimen, the sloped transition surface 53 in the present disclosure is conducive to prevent interference between the press plate 5 and the frame 4, and prevent loading stress from offsetting from center of the rock sample specimen.

During experiment for simulating rockburst, the rock sample specimen 60 has a half or through hole for simulating gallery dredging, therefore, the press plate 5 corresponding to an opening of the half or through hole has a center half hole 56. If the rock sample specimen 60 adopted in the experiment has half hole, only one press plate 5 is required to have the center half hole 56; if the rock sample specimen 60 adopted in the experiment has through hole, a pair of press plates 5 positioned in the same direction (e.g. X direction) is required to have the center half hole 56.

In a embodiment of the present disclosure, a mounting element 57 in a cylindrical shape is fixedly disposed at center of the abutment surface 52 of the press plate 5 having center half hole 56. An light transmission slot 571 is provided at center of the mounting element 57 in which a micro camera 6 is mounted and directed straight towards the center half hole 56 of the press plate 5. The mounting element 57 may be integrally formed with the press plate 5. The specimen box configured in the above structure is adapted to the rock sample specimen 60 having half hole, and the course of rockburst of the rock sample specimen 60 having half hole can be recorded and/or photographed by the micro camera 6. If the rock sample specimen 60 has a through hole, a second mounting element 58 in a cylindrical shape may be fixedly disposed at center of the abutment surface 52 of the other press plate 5 having center half hole 56. A second light transmission slot 581 is provided at center of the second mounting element 58 in which a focus lamp 7 is mounted so as to provide light for the micro camera 6. Both micro camera 6 and focus lamp 7 are directed straight towards the center half hole 56 of the press plate 5. The course of rockburst of the rock sample specimen 60 having through hole can be recorded and/or photographed by the micro camera 6.

Figure 7:
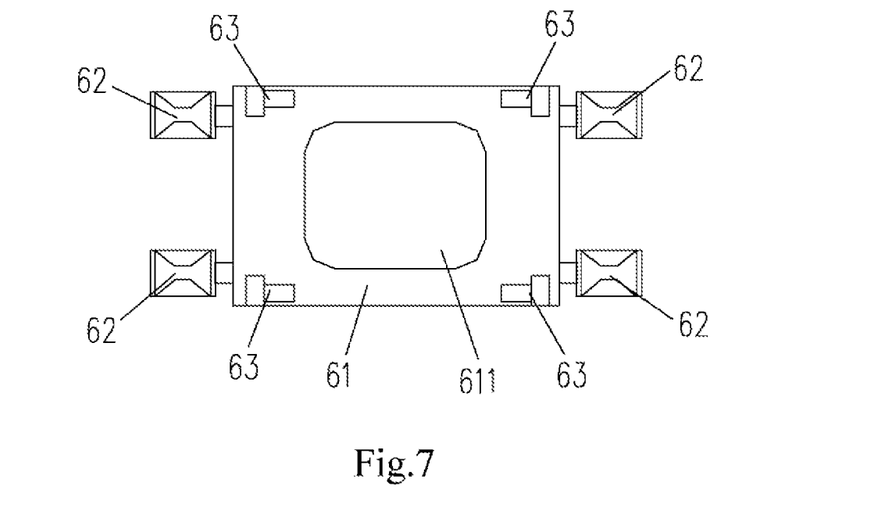
FIG. 7 is a structural schematic view of a specimen box trolley in the specimen box assembly according to the present disclosure.

In an embodiment of the present disclosure, a specimen box trolley is further provided which includes a flat plate 61 and two pairs of wheels 62 mounted at two sides of the flat plate 61. The two pairs of wheels 62 cooperate with lower two of the four X-direction supporting posts 11, or with lower two of the four Z-direction supporting posts 31. The specimen box trolley can also be directly placed on the work platform 103 of the bracket 100 if the space is enough. Before the experiment, the specimen box is mounted to the specimen box trolley, and then the specimen box trolley is mounted to the whole apparatus at a center position which saves labor and is convenient.

In addition, in an embodiment of the present disclosure, if a loading experiment in vertical direction is required, a through hole 611 may be provided at center of the flat plate 61 which is adapted to install a vertical-direction lead screw, such as Y-direction lead screw 25. The through hole 611 may be in a circular shape with a diameter 1-10 mm larger than that of the Y-direction lead screw 25, thereby ensuring the Y-direction lead screw 25 is able to pass through the through hole 611, and the specimen box jacked up by the Y-direction lead screw 25 is centrally located, that is, assisting for positioning in vertical direction, e.g. in Y direction. In the present embodiment, the specimen box is pushed into the apparatus in X direction, therefore, it is focused on whether the position is central in X direction, and the dimension in Z direction has little effect to assist for positioning. To this end, the through hole 611 may be designed in rectangular shape. Distance between a pair of opposite sides in X direction of the through hole 611 may 1-10 mm larger than the diameter of the Y-direction lead screw 25, and distance between a pair of opposite sides in Z direction of the through hole 611 may be slightly larger, such that the Y-direction lead screw 25 is facilitated to pass. Furthermore, if the through hole 611 of the flat plate 61 of the specimen box trolley is designed for a larger specimen box, e.g. a larger specimen box in size of 160*160*160 mm, the dimension of the through hole 611 of the flat plate 61 may be designed according to the above structural requirement. In order to allow the specimen box trolley in the above dimension can also be adapted to a smaller specimen box, e.g. a specimen box in size of 110*110*110 mm, a restricting frame may be detachably or fixedly connected to an inner edge of the through hole 611 of the flat plate 61, and designed that the distance between a pair of opposite sides in X direction of the restricting frame is 1-10 mm larger than the diameter of the Y-direction lead screw 25, which also has a function of assisting the rock sample specimen to be installed at a center position. The explanation to the installation of the rock sample specimen will be described as follows.

Before the experiment, it is required to install the rock sample specimen, the particular operation is as follow. Putting the rock sample specimen into the specimen box, carrying the specimen box onto two X-direction supporting posts 11, and pushing the specimen box trolley into a central position. Firstly, rotating the Y-direction adjusting handle wheel 27, such that the Y-direction lead screw 25 moves upwardly by the cooperation of the Y-direction adjusting handle wheel 27, transmission chain and the operating wheel 26, so that the specimen box is jacked up and separates from the specimen box trolley through the through hole 611. The Y-direction lead screw 25 stops moving upwardly until a head of the piston of the Y-direction loading hydraulic cylinder 24 just passes through the top window of the frame 4 shaped in a cube and contact to the top surface of the rock sample specimen without applying force to the rock sample specimen, then the adjustment in Y direction is finished. During this course, the Y-direction lead screw 25 can jack up the specimen box through the through hole 611 only in case that the specimen box trolley moves to the central position, otherwise, the specimen box can not be jacked up, therefore, the specimen box in the present disclosure has function of assisting for locating for the installation of the specimen box. And then, pushing the first X-direction frame 12 in X axis direction, such that a head at the end of the piston of the X-direction loading hydraulic cylinder just passes through the window of the frame 4 shaped in a cube and contact to the front surface of the rock sample specimen without applying force to the rock sample specimen, at this point, rotating the X-direction adjusting handle wheel 16 to move the X-direction lead screw 15 towards the rock sample specimen until a head at the end of the sensor at the X-direction lead screw 15 contacts to the back surface of the rock sample specimen without applying force to the rock sample specimen, then the adjustment in X direction is finished. Finally, pushing the first Z-direction frame 32 in Z axis direction, such that a head at the end of the piston of the Z-direction loading hydraulic cylinder just passes through the left window of the frame 4 shaped in a cube and contact to the left surface of the rock sample specimen without applying force to the rock sample specimen, at this point, rotating the Z-direction adjusting handle wheel 36 to move the Z-direction lead screw 35 towards the rock sample specimen until a head at the end of the sensor at the Z-direction lead screw 35 contacts to the right surface of the rock sample specimen without applying force to the rock sample specimen, then the adjustment in Z direction is finished. During the installation, the order of X axis direction and Z axis direction adjustment may be reversed. The above courses are accomplished manually, thereafter, it is possible to accurately adjust interrelationship between the rock sample specimen and each head by control systems so as to ensure each head contacts to each surface of the rock sample specimen without applying force to the rock sample specimen.

The simulated impact-type rock burst experiment apparatus according to the present disclosure is powered by conventional power system, and is able to perform various experiments under the automatic or semiautomatic control of the control system, such as experiment simulating an impact rockburst, uniaxial compression experiment, uniaxial tension experiment, shear experiment, experiment of gassy seam blower induced by vibration, fatigue experiment of strain control for low cycle rock, hydrostatic experiment and true triaxial experiment, etc.

Although the present disclosure has been illustrated by referring to several typical embodiments, it should be understood that terms used in the present disclosure are only for illustrative and exemplary purposes, rather than restrictive terms. Since the present disclosure may be implemented concretely in various forms without departing from spirit and substance of the present disclosure, it should be understood that the above embodiments are not limited to any details described above, but should be explained broadly within the spirit and scope defined in appended claims. Therefore, all changes and modifications falling into the claims and their equivalent scope should be looked as being covered by the claims.

What is claimed is:

1. A simulated impact-type rock burst experiment apparatus, comprising:
 a bracket, a specimen box assembly, X-direction, Y-direction and Z-direction loading mechanisms mounted on the bracket, three sets of independent control systems for controlling the X-direction, Y-direction and Z-direction loading mechanisms respectively,
 wherein, the X-direction loading mechanism comprises:
  four X-direction supporting posts in a rectangular arrangement;
  a first X-direction frame mounted on the bracket and fixedly connected to one end of the four X-direction supporting posts;
  a second X-direction frame mounted on the bracket and fixedly connected to the other end of the four X-direction supporting posts and aligned with the first X-direction frame;
  an X-direction loading hydraulic cylinder fixedly mounted at a center position of the first X-direction frame; and
  an X-direction lead screw mounted at a center position of the second X-direction frame with a center line thereof in line with a center line of a piston rod of the X-direction loading hydraulic cylinder, wherein an X-direction adjusting handle wheel is provided at an outer end of the X-direction lead screw, and an X-direction sensor is provided at an inner end of the X-direction lead screw;
 the Y-direction loading mechanism comprises:
  four Y-direction supporting posts in a rectangular arrangement and mounted on the bracket;
  a first Y-direction frame fixedly connected to one end of the four Y-direction supporting posts;
  a second Y-direction frame fixedly connected to the other end of the four Y-direction supporting posts, and aligned with the first Y-direction frame;
  a Y-direction loading hydraulic cylinder fixedly mounted at a center position of the first Y-direction frame; and
  a Y-direction lead screw mounted at a center position of the second Y-direction frame with a center line thereof in line with a center line of a piston rod of the Y-direction loading hydraulic cylinder; wherein an operating wheel is provided at an outer end of the Y-direction lead screw, and a Y-direction sensor is provided at an inner end of the Y-direction lead screw;
 the Z-direction loading mechanism comprises:
  four Z-direction supporting posts in a rectangular arrangement;
  a first Z-direction frame mounted on the bracket and fixedly connected to one end of the four Z-direction supporting posts;
  a second Z-direction frame mounted on the bracket and fixedly connected to the other end of the four Z-direction supporting posts, and aligned with the first Z-direction frame;

a Z-direction loading hydraulic cylinder fixedly mounted at a center position of the first Z-direction frame;

a Z-direction lead screw mounted at a center position of the second Z-direction frame with a center line thereof in line with a center line of a piston rod of the Z-direction loading hydraulic cylinder; wherein a Z-direction adjusting handle wheel is provided at an outer end of the Z-direction lead screw, and a Z-direction sensor is provided at an inner end of the Z-direction lead screw;

wherein extension lines of center lines of piston rods of X, Y and Z-direction loading hydraulic cylinders intersect at a same center point, and the specimen box assembly is disposed on the bracket with a center of the specimen box assembly coincident with the same center point.

2. The simulated impact-type rock burst experiment apparatus according to claim 1, wherein two pairs of X-direction guide rails are provided on the bracket, a pair of first X-direction legs are provided under the first X-direction frame in which a first X-direction roller is mounted under each first X-direction leg; a pair of second X-direction legs are provided under the second X-direction frame in which a second X-direction roller is mounted under each second X-direction leg, the two first X-direction rollers and the two second X-direction rollers cooperate with the two pairs of X-direction guide rails respectively.

3. The simulated impact-type rock burst experiment apparatus according to claim 1, wherein two pairs of Z-direction guide rails are provided on the bracket, a pair of first Z-direction legs are provided under the first Z-direction frame in which a first Z-direction roller is mounted under each first Z-direction leg; a pair of second Z-direction legs are provided under the second Z-direction frame in which a second Z-direction roller is mounted under each second Z-direction leg, the two first Z-direction rollers and the two second Z-direction rollers cooperate with the two pairs of Z-direction guide rails respectively.

4. The simulated impact-type rock burst experiment apparatus according to claim 1, wherein the bracket comprises a base and a work platform in a horizontal state and fixedly mounted on the base by a post, the first X-direction frame, the second X-direction frame, the four Y-direction supporting posts, the first Z-direction frame and the second Z-direction frame are mounted on the work platform, and the second Y-direction frame is located in a space between the work platform and the base.

5. The simulated impact-type rock burst experiment apparatus according to claim 1, wherein the Y-direction supporting posts are arranged in vertical direction with lower ends thereof pass through the bracket; nuts are respectively engaged with lower parts of the Y-direction supporting posts; compression springs are respectively sleeved around the lower parts of the Y-direction supporting posts with an upper end against the nut and a lower end against the bracket.

6. The simulated impact-type rock burst experiment apparatus according to claim 1, wherein a Y-direction adjusting handle wheel is provided at a side surface of the second Y-direction frame, which is coupled with the operating wheel through a transmission chain.

7. The simulated impact-type rock burst experiment apparatus according to claim 1, wherein the control system comprising:

a plurality of sensors used for collecting displacement, amount of deformation of or value of force acting on the rock sample specimen, respectively;

a hydraulic source comprising a pump station used for supplying hydraulic oil for X, Y and/or Z-direction loading hydraulic cylinders, and a servo valve comprising at least one adjusting valve and at least one reversal valve; and a controller used to equalize the displacement of or force acting on each piston rod of X, Y and/or Z-direction loading hydraulic cylinders and amount of force, displacement or deformation represented by the input dynamic load signal, by receiving data collected by the plurality of sensors, evaluating difference by comparing the received data with a given dynamic load signal, performing correction adjustment based on the difference to control opening amount of the adjusting valve, and in turn to control the amount and rate of oil intake or oil output of X, Y and/or Z-direction loading hydraulic cylinders to further control displacement of or force acting on each piston rod of X, Y and/or Z-direction loading hydraulic cylinders, and controlling the reversal valve to reverse.

8. The simulated impact-type rock burst experiment apparatus according to claim 1, wherein the specimen box assembly comprises a frame and 6 press plates, the frame is composed of 12 arrises for housing a rock sample specimen and in a shape of cube or rectangular parallelepiped;

the 6 press plates correspond to the 6 windows of the frame respectively;

each press plate comprises a press plate body having a loading surface towards the interior of the frame and an abutment surface opposite to the loading surface, the dimension of the loading surface of the press plate is smaller than that of the window of the frame;

one hitch is formed at a center of each peripheral side of the press plate, one restricting element is provided at a center of each arris of the frame, and the press plate is hitched to the frame through the hitch and the restricting element.

9. The simulated impact-type rock burst experiment apparatus according to claim 8, wherein the dimension of the abutment surface is larger than or equal to that of the window of the frame; and each loading surface of the press plate body has a sloped transition surface at the periphery.

10. The simulated impact-type rock burst experiment apparatus according to claim 8, wherein the specimen box assembly further comprises 6 friction reducing plates located between the 6 press plates and the rock sample specimen respectively, the friction reducing plate has a thickness of 1-2 mm.

11. The simulated impact-type rock burst experiment apparatus according to claim 8, wherein one of the 6 press plates has a center half hole corresponding to an opening of a half hole on the rock sample specimen.

12. The simulated impact-type rock burst experiment apparatus according to claim 10, wherein a mounting element is disposed at center of the abutment surface of the press plate having a center half hole; a light transmission slot is provided at the mounting element in which a micro camera is mounted and directed straight towards the center half hole of the press plate.

13. The simulated impact-type rock burst experiment apparatus according to claim 8, wherein a pair of press plates of 6 press plates positioned in a same direction has a center half hole respectively corresponding to openings of a through hole in the rock sample specimen.

14. The simulated impact-type rock burst experiment apparatus according to claim 13, wherein a mounting element is disposed at center of the abutment surface of one of the pair of press plates having center half hole; a light transmission slot is provided at the mounting element in which a micro camera is mounted; a second mounting element is disposed at center of the abutment surface of the other one of the pair of press plates having center half hole; a second light transmission slot is provided at the second mounting element in which a focus lamp is mounted, both the micro camera and the focus lamp are directed straight towards the center half hole of the press plate.

15. The simulated impact-type rock burst experiment apparatus according to any one from claim 8, wherein the specimen box assembly further comprises a specimen box trolley which comprises a flat plate and two pairs of wheels mounted at two sides of the flat plate; the two pairs of wheels cooperate with two of the four X-direction supporting posts in lower position, or with two of the four Z-direction supporting posts in lower position.

16. The simulated impact-type rock burst experiment apparatus according to claim 15, wherein a through hole is provided at center of the flat plate which is adapted to install a vertical direction lead screw.

17. The simulated impact-type rock burst experiment apparatus according to claim 16, wherein the through hole of the flat plate is in a circular shape with a diameter 1-10 mm larger than that of the vertical-direction lead screw.

18. The simulated impact-type rock burst experiment apparatus according to claim 16, wherein the through hole is in rectangular shape, and distance between a pair of opposite sides of the through hole is 1-10 mm larger than the diameter of the vertical-direction lead screw.

19. The simulated impact-type rock burst experiment apparatus according to claim 16, wherein a restricting frame is mounted at an inner edge of the through hole on the flat plate of the specimen box trolley, and a distance between a pair of opposite sides of the restricting frame is 1-10 mm larger than a diameter of the vertical direction lead screw.

* * * * *